US006093758A

United States Patent [19]
Allcock et al.

[11] Patent Number: 6,093,758
[45] Date of Patent: Jul. 25, 2000

[54] PHOSPHORYLATION OF PHOSPHAZENES

[75] Inventors: Harry R. Allcock; Jonathan R. Taylor, both of State College, Pa.

[73] Assignee: The Penn State Research Foundation, University Park, Pa.

[21] Appl. No.: 09/334,246

[22] Filed: Jun. 16, 1999

Related U.S. Application Data

[60] Provisional application No. 60/089,690, Jun. 17, 1998.

[51] Int. Cl.$^7$ .......................... C08K 5/5399; C07F 9/24
[52] U.S. Cl. ......................... 524/116; 524/122; 558/80; 558/93; 558/157
[58] Field of Search .............................. 558/80, 93, 157; 524/116, 122

[56] References Cited

U.S. PATENT DOCUMENTS

| | | | |
|---|---|---|---|
| 3,462,518 | 8/1969 | Kober et al. ........................... | 558/80 |
| 3,865,783 | 2/1975 | Clutter . | |
| 3,883,451 | 5/1975 | Reynard . | |
| 3,890,092 | 6/1975 | Garner . | |
| 3,986,882 | 10/1976 | Franko-Ffilipasic et al. . | |
| 4,002,596 | 1/1977 | Murch . | |
| 4,042,561 | 8/1977 | DeEdwardo et al. . | |
| 4,061,606 | 12/1977 | Dieck et al. . | |
| 4,079,035 | 3/1978 | Brackenridge et al. . | |
| 4,083,820 | 4/1978 | Dieck et al. . | |
| 4,117,041 | 9/1978 | Gruschl . | |
| 4,182,836 | 1/1980 | Hergenrother . | |
| 4,405,738 | 9/1983 | McNeely . | |
| 4,607,077 | 8/1986 | Silver et al. . | |
| 5,024,860 | 6/1991 | Chang . | |
| 5,652,285 | 7/1997 | Coggio et al. . | |

OTHER PUBLICATIONS

Allcock, Advanced Materials, 1994, 6,106.
Bowmer et al, Macromolecules 1991, 24,4827.
Alcock et al, Chem. Mater., 1990, 2,425.
Peddada et al, Macromolecules 1983, 16, 1258.
Reed et al, Chem. Mater. 1996, 8,440.
Kourtides, J. Fire Sciences 1983, 1, 200.
Lieu et al, J. fie flammability, 1980, 11, 167.
Fewell,. Fire flammability 1979, 10,274.
Honeyman et al, Ambient Temperature synthesis of Poly-(dichlorphosphazene) with Molecular Weight Control, J. Am. Chem. Soc., 1995, 117.
Burton et al, Phosphate Substituted Phosphazenes As Dispersants in colloidal Ceramic Processing, mat. Res. Soc. Symp. Proc., vol. 249, 1992.
Liu et al., Synthesis and Flame–Retardant Properties of Phosphorous–Containing Polymers Based on Poly(4–hydroxystryrene), J. Appl. Polym. Sci., 1996, 59, 1619.
Godfrey et al., Ind. Eng. Chem. Prod. Res. Develop, 1970, 9,246.
Weil, Encycl. Polym. Sci. Technol., 1988, 10,976.
Baillet et al, Polym. Deg. Stab., 1992, 37,149.
Boutevin et al, Polym. Bull., 1993, 30,243.
Troev, K. et al; D. M. J. Polym. Sci., Part A: Polym. Chem. 1996, 34, 621.
Camino, G. et al.; Reviews in Inorganic Chemistry 1986, 8, 69.
Banks, M.et al.; Polymer 1994, 35, 3470.
Banks, M. et al.; Polymer 1993, 34, 4547.
Reghunadhan Nail C. P. et al.; Polym. Deg. Stab. 1989, 26, 305.
Burton, S. D.et al.; J. M. Mat. Res. Soc. Symp. Proc. 1992, 249, 267.
Emblem, H. G.et al.; Polym. Jr. 1972, 4, 103.
Medici, A.et al.; Macromolecules 1992, 25,2569.
Allcock, H. R.et al.; Macromolecules 1980, 13, 1325.
Nelson, G. L., Ed. Fire and Polymers II•Materials and Tests for Hazard Prevention, Symposium, 599, ACS, Washington, D.C. 1994; pp. 580–592.
von Gentzkow, W.et al.; Makromol. Chem, Macromol. Syrup. 1993, 74, 173.
Allcock, H. R.et al.; Chem. Mater. 1993, 5, 1307.
Green, J., J. Fire Sciences. 1996, 14, 353.
Nishihara, H.et al.; Polym. J. 1998, 30, 163.
Corbridge, D. E. C. Phosphorus, 5th ed., Elsevier: New York, 1995., pp.
Emsley, J.et al.; The Chemistry of Phosphorus, John Wiley and Sons: New York, 1976., pp.
Hudson, R. F. Structure and Mechanism in Organo–Phosphorus Chemistry,. Academic Press: New York, 1965., pp.

*Primary Examiner*—Michael G. Ambrose
*Attorney, Agent, or Firm*—Thomas J. Monahan

[57] ABSTRACT

Incorporation of phosphate and phosphonate units into the side groups of aryloxyphosphazenes, at both the polymer and cyclic trimer levels, is disclosed. Phosphorylated cyclic trimers are utilized as flame-retardant additives to polystyrene.

38 Claims, No Drawings

PHOSPHORYLATION OF PHOSPHAZENES

The benefit of priority to U.S. provisional patent application No. 60/089,690 filed Jun. 17, 1998 is claimed.

BACKGROUND OF THE INVENTION

The thermal behavior and decomposition of polyphosphazenes have been studied in the art. See, for example, Bowmer et al., *Macromolecules* 1991, 24, 4827. At elevated temperatures, thermal behavior of phosphazenes depends on the types of side groups present. Specific side groups on the polyphosphazene can lead to crosslinking, or to depolymerization to cyclic oligomers. Both of these processes can affect the fire retardant properties of the polyphosphazenes. See, for example, Kourtides, D., *J. Fire Sciences,* 1983, 1, 200.

Phosphazenes are known for use as flame retardant additives in organic polymeric mixtures. Polymeric mixtures are obtained through curing reactions between the host organic polymer and functional side groups on the polyphosphazene. See, for example, U.S. Pat. No. 5,024,860. Polymeric mixtures which contain cyclic trimers and tetramers are known for use as flame retardant polyaramids, polyesters, and rayon. Except for rayon formulations, aryloxyphosphazenes are preferred due to their superior thermal stability. In all of these mixtures, the side groups on the phosphazene are chosen to maximize flame retardancy while providing miscibility and/or reaction with the host polymer. Flame retardancy is commonly attributed to generation of polyphosphoric acid and subsequent char formation, or to a modification of the decomposition mechanism of the polymer. See, for example, Weil, E. D., Encycl. Polym. Sci. technol. 1988, 10, 976.

One of the reasons phosphazenes have excellent flame retardant properties is the presence of phosphorus in the backbone. The art has made significant effort to incorporate phosphorus by use of small molecule or polymeric additives, copolymerizations, and chemical modification. The effectiveness of phosphorus compounds chemically bonded to an organic polymer varies with location—whether randomly distributed, isolated into blocks, or pendent to the main chain. See Reghunadhan Nair, C. P., et al., *Polym. Deg. Stab.* 1989, 26, 305. For example, the art shows phosphazenes bearing phosphate, phosphonate, and phosphine oxide side groups which utilize alkyl and alkoxide ligands. These phosphazenes, however, do not have satisfactory thermal stability.

A need therefore exists for polyphosphazenes which have improved thermal stability and which are useful as flame retardants in a wide range of polymers.

SUMMARY OF THE INVENTION

Aryloxyphosphazenes bearing functionalized aryloxy side groups, hydroxy functionalized aryloxy side groups, are phosphorylated by reaction with halogenated phosphate esters, preferably ethyl chlorophosphate and phenyl chlorophosphate.

The invention advantageously can produce phosphorylated polymers which have thermal stability superior to that of non-phosphorylated phosphazenes. The phosphorylated phosphazenes of the invention, preferably phosphorylated aryloxy-hydroxy functionalized cyclic trimer phosphazenes, can be employed as flame retardant additives to improve fire resistance of organic polymers such as polystyrene.

Manufacture of phosphorylated phosphazenes having improved thermal stability entails reacting an aryloxy-hydroxy functional phosphazene with a halogenated chlorophosphate such as aliphatic chlorophosphates and aromatic chlorophosphates. The aryloxy-hydroxy functional phosphazene is preferably Hexakis(4-hydroxyphenoxy) cyclotriphosphazene, poly[bis(4-hydroxyphenoxy) phosphazene] and mixtures thereof. The aliphatic chlorophosphate may be any of alkyl chlorophosphates, C1–C6 straight chain aliphatic chlorophosphates, C1–C6 branched aliphatic chlorophosphates, and C1–C6 cyclic aliphatic chlorophosphates, alkyne chlorophosphate such as any of C3–C8 alkyne chlorophosphates, and alkene chlorophosphates such as any of C3–C8 alkene chlorophosphate. Preferably, the alkyl chlorophosphate is ethyl chlorophosphate.

The aromatic chlorophosphates may be any of phenyl chlorophosphate, C1–C6 alkyl substituted phenyl chlorophosphate, C3–C8 alkyne substituted phenyl chlorophosphate, and C3–C8 alkene substituted phenyl chlorophosphate, preferably phenyl chlorophosphate.

The invention also relates to organic polymeric mixtures having improved fire resistance. These mixtures include an organic polymer, preferably polystyrene, and a phosphorylated phosphazene. The phosphorylated phosphazene is the reaction product of a halogenated chlorophosphate selected from the group consisting of aliphatic chlorophosphate and an aryloxy-hydroxy functional phosphazene. The aryloxy-hydroxy functional phosphazene is any of hexakis(4-hydroxyphenoxy)cyclotriphosphazene, poly[bis(4-hydroxyphenoxy)phosphazene], and mixtures thereof. The aliphatic chlorophosphate is any of alkyl chlorophosphates such as C1–C6 straight chain aliphatic chlorophosphates, C1–C6 branched aliphatic chlorophosphates, and C1–C6 cyclic aliphatic chlorophosphates, alkyne chlorophosphate such as C3–C8 alkyne chlorophosphates, and alkene chlorophosphates such as any one of C3–C8 alkene chlorophosphates. Preferably, the alkyl chlorophosphate is ethyl chlorophosphate and the aromatic chlorophosphates is phenyl chlorophosphate. Other aromatic chlorophosphates which may be used include C1–C6 alkyl substituted phenyl chlorophosphate, C3–C8 alkyne substituted phenyl chlorophosphate, and C3–C8 alkene substituted phenyl chlorophosphate.

Having summarized the invention, the invention will now be described in detail by reference to the following description and non-limiting examples.

DETAILED DESCRIPTION OF THE INVENTION

Equipment
1. Bruker WM-360 NMR spectrometer resonating at 90.56 MHZ, 360.13 MHZ, and 145.81 MHZ respectively is used to obtain $^{13}$C, $^1$H, and $^{31}$P NMR spectra.
2. Mattson Instruments Galaxy Series FTIR 3000 is used to obtain infrared spectra.
3. Parr hydrogenator utilizing 2 atm pressure of hydrogen gas and catalyzed by 10% palladium supported on carbon is used to accomplish hydrogenation reactions.
4. Hewlett-Packard HP1090 gel permeation chromatograph equipped with a HP-1037A refractive index detector and a Polymer Laboratories PL gel 10 gm column calibrated with polystyrene standards (Waters) is used to obtain molecular weights. Samples are eluted with a 0.1 wt % solution of tetra-n-butylammonium nitrate in THF.

Materials
1. Hexachlorocyclotriphosphazene (Ethyl Corp./Nippon Fine Chemical Co.) is purified by recrystallization from heptane followed by sublimation at 50° C. (0.05 mm Hg).

2. Poly(dichlorophosphazene) (0.75 M solution in cyclohexane, Ethyl Corp.) is used as received.
3. Tetrahydrofuran (THF), dioxane, and triethylamine are dried over sodium benzophenone ketyl and distilled under a nitrogen atmosphere.
4. Dichloromethane and chloroform are dried over calcium hydride and distilled under a nitrogen atmosphere.
5. Sodium hydride (60% dispersion in mineral oil), tetra-n-butyl ammonium bromide, 4-benzyloxyphenol, 4-bromophenol, n-butyllithium (1.6 M solution in hexanes), boron tribromide (1.0 M solution in dichloromethane), diethyl chlorophosphate, diphenyl chlorophosphate, triphenyl phosphate, and polystyrene (average Mw 280,000 GPC) are obtained from Aldrich and used as received.
6. Methyl ethyl ketone (MEK) is obtained from Fisher and used as received.
7. CuCl (Aldrich) is precipitated from concentrated HCl, washed with ethanol and diethyl ether and stored over $P_2O_5$.
8. 4-Methoxyphenol (Aldrich) is sublimed at room temperature (0.05 mm Hg).

Synthesis of Phosphazenes

The following phosphazene compounds 1–7 are prepared as described below:

Compound 1

Hexakis(4-benzyloxyphenoxy)cyclotriphosphazene $(N_3P_3(OC_6H_4OC_7H_7)_6)$

A suspension of 20.00 g ($5.74 \times 10^{-2}$ mol) of hexachlorocyclotriphosphazene, 22.99 g (0.57 mol) of NaH 60% oil dispersion, and 1.5 g of tetrabutylammonium bromide in 200 mL of THF is treated with 115.1 g (0.57 mol) of 4-(benzyloxy)phenol in 250 mL of THF. This treatment is performed dropwise, waiting each time for hydrogen evolution. The reaction mixture is successively refluxed for 48 hrs, cooled to room temperature, and ultracentrifuged at 8000 rpm to separate the liquid from the solid. The liquor is evaporated to dryness with a rotovap. The solid brown paste obtained is treated successively with methanol to obtain a white powder which is isolated by filtration, thoroughly washed with water and methanol, and dried. The resulting Hexakis(4-benzyloxyphenoxy)cyclotriphosphazene trimer is purified by multiple crystallizations from 50% THF/$CH_3OH$ mixtures.

Compound 2

Hexakis(4-hydroxyphenoxy)cyclotriphosphazene $(N_3P_3(OC_6H_4OH)_6)$

A solution of 1.74 mL ($1.8 \times 10^{-2}$ mol) of boron tribromide in anhydrous $CH_2Cl_2$ (30 mL) is treated dropwise with a solution of 2.18 g ($3 \times 10^{-3}$ mol) of Hexakis(4-benzyloxyphenoxy)cyclophosphazene in anhydrous $CH_2Cl_2$ (50 mL). The reaction mixture is stirred at room temperature for 3 hours and successively poured into 50 mL of water. A white solid is collected by filtration, washed several times with water, and dried.

Compound 3

Poly[bis(4-benzyloxyphenoxy)phosphazene] ([NP $(OC_6H_4OC_7H_7)_2]_n$)

A suspension of 19.15 g of NaH 60% oil dispersion and 2 g of tetrabutylammonium bromide in 150 mL of dioxane is treated dropwise with a solution of 4-(benzyloxy)phenol (103.60 g) in 300 mL of dioxane. After hydrogen evolution ceased, the mixture is refluxed overnight.

The suspension is successively filtered under nitrogen, via Schlenk technique, directly into a solution of poly (dichlorophosphazene) (15 g (0.13 mol)) in 200 mL of dioxane and is refluxed for 48 hrs. the reaction mixture is cooled to room temperature and poured into a large excess of water. The recovered white polymer is successively purified by multiple dissolutions in THF and reprecipitations in water (three times), methanol (twice), and n-heptane (once).

Compound 4

Poly[bis(4-methoxyphenoxy)phosphazene] ([NP $(OC_6H4OCH_3)_2]_n$)

A solution containing 200 mL of bis(2-methoxyethyl) ether, 100 mL benzene and 22.3 g (0.18 mole) of p-methoxyphenol is prepared and dried by removal of 30 mL of benzene using a Dean-Stark trap. After cooling to room temperature, 4.0 g (0.17 mole) of sodium is slowly added under argon and allowed to react overnight. Additional benzene is distilled to remove traces of water. A solution containing 9.1 g (0.08 mole) of poly(dichlorophosphazene) in 125 mL of toluene is slowly added under argon over a period of 1 hr to the sodium p-ethylphenoxide solution at 90° C. The reaction became increasingly viscous during addition and resulted in a thick suspension. The reaction temperature is raised to 115° C. by further removal of benzene and maintained at 115° C. for 18 hr. A constant titer is obtained during this interval by removing aliquots from the reaction and titrating against dilute hydrochloric acid. The reaction is cooled and added dropwise to several liters of methanol, to precipitate poly[bis(p-methoxy-phenoxy)phosphazene]. The polymer is washed with water and methanol to remove sodium chloride and excess p-methoxyphenol. The polymer is dissolved in 1 L of tetrahydrofuran, filtered, and precipitated into several liters of methanol. The polymer is redissolved in 600 mL of chloroform, filtered, and reprecipitated into several liters of methanol. After a final wash with methanol, the polymer is dried under vacuum (25° C., 0.1 mm) to give 13 g of poly[bis(p-methoxyphenoxy) phosphazene (56%).

Compound 5

Hexakis(4-bromo-phenoxy)cyclotriphosphazene $(N_3P_3(OC_6H_4Br)_6)$

A sample of p-bromophenol (67.9 g, 0.393 mol) is dissolved in THF (300 mL), and the resulting solution is added dropwise to a stirred suspension of sodium hydride (31.2 g, 1.30 mol) and THF (100 mL) at 0 C. After 1 hour, the reaction mixture is filtered (under nitrogen) and the filtrate transferred to a reaction vessel (10000 mL capacity) equipped with an a addition funnel, a water-cooled condenser, and a nitrogen inlet. A solution of $(NPCl_2)_x$(10 g, 0.0287 mol) in THF (100 mL) is then added dropwise. Following the complete addition of the solution of $(NPCl_2)$, the reaction mixture is allowed to boil at reflux for 168 hours. Isolation of the product is accomplished by removal of the reaction solvent by means of a rotary evaporator and by treatment of the residue with dilute aqueous hydrochloric acid. The solid is collected by filtration and then washed sequentially with ethanol (100 mL) and with hexane (100 mL). Analytically pure samples of $(N_3P_3(OC_6H_4Br)_6)$ are obtained by recrystallization from acetone.

Compound 6

Poly[bis(4-bromo-phenoxy)phosphazene] ([NP(OC$_6$H$_4$Br)$_2$]n)

A solution of sodium p-bromophenoxide in dioxane is prepared by adding a solution of p-bromophenol in dioxane (100 mL) to a stirred suspension of a molar excess of sodium hydride and dioxane (100 ML). This solution is heated to reflux and filtered into a reaction vessel (three-necked, 1-L capacity). A solution of poly(dichlorophosphazene) in dioxane (150 mL) is added dropwise to the sodium p-bromophenoxide solution at reflux. The reaction mixture is heated at reflux for 168 hr and concentrated by rotoevaporation, and the concentrated added to water. The precipitate is washed with ethanol. The polymer is dissolved in boiling dioxane. The hot solution is filtered and reprecipitated into water. The recovered ([NP(OC$_6$H$_4$Br)$_2$]n) polymer is redissolved in boiling dioxane and reprecipitated once again into water. The polymer is further reprecipitated from dioxane into ethanol and then from dioxane into pentane.

Compound 7

Poly[bis(4-hydroxyphenoxy)phosphazene] ([NP(OC$_6$H$_4$OH)$_2$]n from Compound 3.

Compound 3 (10.0 g) is dissolved in 1.5 L CH$_2$Cl$_2$, and 45.1 mL BBr$_3$ solution (1 eq) is added slowly via syringe. The resulting deprotected polyphosphazene precipitated from solution within a few minutes, and the reaction is quenched by pouring the reaction mixture into 2 L of distilled water after 30 minutes. The resulting poly[bis(4-hydroxyphenoxy)phosphazene] product is vacuum filtered, washed with distilled water, and purified by dialysis against methanol. Yield: 2.7 g (45%) $^{31}$P NMR (d$_4$-methanol)δ-17.4 ppm; $^1$H NMR (d$_4$-methanol) δ 6.5 ppm (4H, Ar AA' BB'); $^{13}$C NMR (d4-methanol) δ 154.0, 146.2, 123.6, 116.4 ppm (Ar); IR (cm$^{-1}$): 3280, 3200–3000, 1613, 1511, 1363, 1254, 1203, 953, 844. T$_g$=90° C. Mw=14,328; M$_n$=6,559; M$_w$/M$_n$=2.19 (The molecular weight is determined after conversion to poly[bis(p-acetyloxy phenoxy)phosphazene] by acetylation of Poly[bis(4-hydroxyphenoxy)phosphazene].

Acetylation of Poly[bis(4-hydroxyphenoxy)phosphazene] is accomplished by forming a solution of 1.12 g of Poly[bis(4-hydroxyphenoxy)phosphazene] in 5 mL of dry pyridine. This solution is treated with 1.44 mL (1.5×10$^{-2}$ mol) of acetic anhydride. After 2 hrs of stirring, the reaction mixture is poured into 50 mL of a 5% aqueous HCL solution. A white solid is collected, washed with water, filtered, and dried.

Compound 7

Poly[bis(4-hydroxyphenoxy)phosphazene] ([NP(OC$_6$H$_4$OH)$_2$]$_n$) from compound 4.

Compound 4 (4.0 g) is dissolved in 900 mL CHCl$_3$, and 34.3 mL BBr$_3$ solution (2 eq) is added slowly via syringe. The resulting deprotected polyphosphazene precipitated from solution after 30 minutes, and the reaction is quenched by pouring the reaction mixture into 2 L of distilled water after 2.5 hours. The resulting poly[bis(4-hydroxyphenoxy) phosphazene] product is vacuum filtered, washed with distilled water, and purified by dialysis against methanol. Yield: 2.0 g (55%)of a white solid of having the same characterization data as above.

Phosphorylation of Hydroxy Functionalized Phosphazenes

Phosphorylation of hydroxy functionalized phosphazenes such as compounds 2 and 7 to yield compounds 8–11 below is performed using the following general reaction scheme 1.

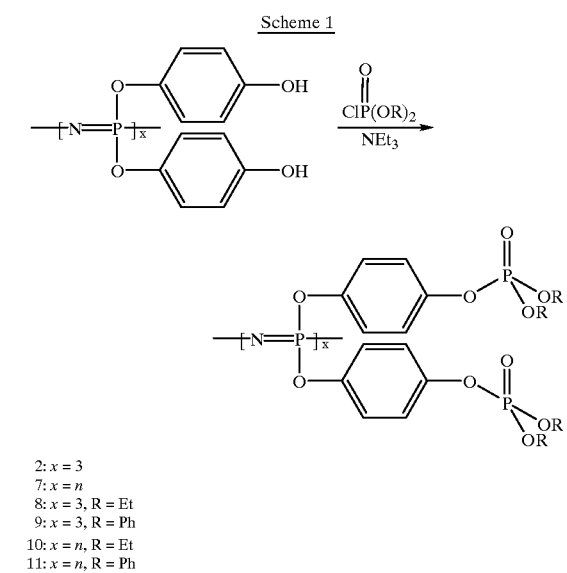

Scheme 1

2: $x = 3$
7: $x = n$
8: $x = 3$, R = Et
9: $x = 3$, R = Ph
10: $x = n$, R = Et
11: $x = n$, R = Ph where R in

is —CH$_2$CH$_3$ or —C$_6$H$_5$; Et is ethyl, and Ph is phenyl.

In scheme 1, ClPO(OCH$_2$CH$_3$)$_2$ or ClPO(C$_6$H$_5$) each can be reacted with phosphazenes. It is to be understood, however, that mixtures of halogenated phosphates such as mixtures of ClPO(OCH$_2$CH$_3$)$_2$ and ClPO(C$_6$H$_5$) may be reacted with aryloxy-hydroxy functionalized phosphazenes to yield phosphorylated phosphazenes. In addition, mixtures of chlorophosphates may be reacted with aryloxy-bromo functionalized phosphazenes.

Aryloxyphosphazenes, both cyclic and polymeric, which bear pendent phosphate and phosphonate groups are preferred phosphazenes for phosphorylation. In phosphorylation of phosphazenes by reaction with halogenated phosphates as described in scheme 1, diethyl chlorophosphate and diphenyl chlorophosphate preferably are employed, most preferably diphenyl chlorophosphate.

Compound 8

Phosphorylation of Compound 2 with diethyl chlorophosphate to produce N$_3$P$_3$(OC$_6$H$_4$OP(O)(OCH$_2$CH$_3$)$_2$)$_6$ The cyclic trimer compound 2 (1.00 g) is dissolved in 50 mL THF, and 1.4 mL (2 eq) of triethylamine is added. The solution is cooled to 0° C., and then 0.01 g CuCl is added. A solution of 2.62 g (2 eq) diethyl chlorophosphate in 10 mL THF is added dropwise. The mixture is maintained at 0° C. for 3 hours, allowed to warm to room temperature, and then refluxed for 48 hours. After completion of the reaction, the mixture is concentrated by rotary evaporation and treated with a large excess of distilled water. The resulting brown, oily product is redissolved in THF and treated with water twice and hexane twice and then dried under vacuum. The resulting mixture of fully and partially phosphorylated product is treated with a stoichiometric amount of NaH in THF to make the sodium salt of the residual phenolic groups. The reaction mixture is concentrated by rotary evaporation, treated with water, and then with hexane and subsequently dried. Yield: 1.0 g (50%), $^{31}$P NMR (CDCl$_3$) δ 9.7, 9.4, 9.0 ppm (P=N), −5.6, −5.9 ppm ((RO)$_3$P=O); $^1$H NMR (CDCl$_3$) δ 7.0 ppm (4H Ar AA' BB'), 4.2 ppm (4H, m, OCH$_2$—), 1.3 ppm (6H, m, CH$_3$); $^{13}$C NMR (CDCl$_3$) δ 147.8, 147.2, 121.9, 120.9 ppm (Ar), 64.6 ppm (OCH$_2$—), 16.0 ppm (CH$_3$). IR (cm$^{-1}$): 3055, 2987, 1499, 1265, 1171, 1034, 957, 739. MH$^+$=1606.

Compound 9

Phosphorylation of Compound 2 with diphenyl chlorophosphate to produce N$_3$P$_3$(OC$_6$H$_4$OP(O)(OC$_6$H$_5$)$_2$)$_6$ Cyclic trimer compound 2 (0.50 g) is dissolved in 30 mL THF, and 1 mL (2 eq) of triethylamine is added. The solution is cooled to 0° C., and then 0.01 g CuCl is added. A solution of 2.04 g (2 eq) diphenyl chlorophosphate in 10 mL THF is added dropwise. The mixture is maintained at 0° C. for 3 hours, allowed to warm to room temperature, and then refluxed for 24 hours. After completion of the reaction, the mixture is concentrated by rotary evaporation and is treated with a large excess of distilled water. The brown, oily product is redissolved in THF and treated with water twice and hexane twice. After low temperature precipitation from 3:1 ethanol/hexane, the product is dried under vacuum. Yield: 0.8 g (60%). $^{31}$P NMR (CDC$_{13}$) δ 9.2 ppm (P=N), −16.9 ppm ((RO)$_3$P=O); $^1$H NMR (CDCl3)δ 7.3 ppm(4H, m, Ar), 7.2 ppm (5H, m, Ar), 7.0 ppm (4H Ar AA' BB'); $^{13}$C NMR (CDCl$_3$) δ 150.3, 147.5, 129.9, 125.7, 122.1, 121.2, 120.0 (Ar). IR (cm$^{-1}$): 3072, 1591, 1491, 1302, 1163, 957, 771. MH+=2184.

Compound 10

Phosphorylation of Compound 7 with diethyl chlorophosphate to yield [N=P(OC$_6$H$_4$OP(O)(OCH$_2$CH$_3$)$_2$)$_2$]$_n$ Compound 7 (1.00 g) is dissolved in 200 mL THF, and 1.6 mL (1.5 eq) of triethylamine is added. The solution is cooled to 0° C., and then 0.01 g CuCl is added. A solution of 2.62 g (2 eq) diethyl chlorophosphate in 20 mL THF is added dropwise. The mixture is maintained at 0° C. for 3 hours and is then allowed to warm to room temperature. The resulting product is a white solid that precipitated as the temperature approached 25° C. This solid is insoluble, but dispersed in THF, dioxane, DMF, N-methyl pyrrolidone, CHCl$_3$, and CH$_2$Cl$_2$. The solid is washed with heating with THF, dioxane, DMF, and washed at room temperature with benzene. Yield: 0.7 g of a brown solid. IR (cm$^{-1}$): 3300–2500, 1517, 1382, 1273, 1197, 1000, 959, 838.

In phosphorylation of hydroxy functionalized phosphazenes as described above, reaction scheme 1 advantageously can control the functionality of the phosphazene polymer at two stages. In the first stage, as described, for example, in preparation of compound 7, a deprotected phosphazene is prepared by reacting the phosphazene with boron tribromide. The extent of deprotection can be controlled by the amount of boron tribromide reacted with that phosphazene. In the second stage, the deprotected phosphazene is reacted with chlorophosphate to yield a phosphorylated phosphazene. In the second stage, the amount of chlorophosphate reacted with the deprotected phosphazene can be varied to control the amount of phosphate groups in the phosphorylated phosphazene product. The invention thus advantageously enables production of phosphorylated aryloxy hydroxy-functionalized phosphazene polymers having a wide range of amounts of protected functional groups, hydroxyl groups, and phosphate groups.

In reaction of polyphosphazenes such as compound 2 with diphenyl chlorophosphate to produce compound 9, phosphorylation is about 95% complete by the time the reaction mixture has warmed to room temperature. Only a short reflux time of 24 hours is necessary to react all of the hydroxyl groups. Although, in principle, it is intended that all of the hydroxyl functionality be reacted, it should be understood that 100 percent complete reaction cannot always be attained, and therefore, trace amounts of unreacted hydroxyl species should not be considered as outside the scope of the invention. Alternatively, reacting "all" of the hydroxyl for the purposes of the present invention may be defined as at least 99 percent complete reaction, preferably 100 percent.

In the above phosphorylations of aryloxy-hydroxy functional phosphazenes, phosphorylation of compound 2 with ethyl chlorophosphate to yield compound 8 shows about 50% substitution based on $^{31}$P NMR integration analysis after the reaction mixture had warmed to room temperature. Refluxing can be used to increase the amount of conversion.

Phosphorylation of compound 2 is detected by comparison of the IR spectra of phosphorylated compounds 8 and 9 with the spectra of compound 2. In the IR spectra of both compound 8 and compound 9, the O—H stretch at 3300 cm$^{-1}$ had disappeared, which shows full reaction of the hydroxyl functionality of starting phosphazene trimer compound 2. The P=O stretch for the phosphorylated phosphazene of compound 8 is detected as an increase in the intensity of the P=N stretch at 1265 cm$^{-1}$. The (O)P—O—C stretch (C=aliphatic) appeared as a new peak at 1034 cm-1. The P=O stretch for compound 9 is evident as a shifting of the P=N/P=O peak to 1302 cm$^{-1}$.

Phosphorylation of compound 7 with diethyl chlorophosphate to yield compound 10 gave a crosslinked material that precipitated from solution at room temperature. Phosphorylation is indicated by a decrease of the O—H band at 3300 cm$^{-1}$, the appearance of the P=O band at 1273 cm$^{-1}$, and the appearance of the (O)P—O—C (C=aliphatic) band at 1010 cm$^{-1}$. A broad peak at 3200–2500 cm$^{-1}$ is also detected, which indicates a hydrolysis of the phosphate ester unit to P(O)OH groups.

Phosphorylation of compound 7 with diphenyl chlorophosphate to yield compound 11 is complete by the time this system warmed to room temperature, with full substitution indicated by $^{31}$P NMR spectroscopy. Compound 11 is soluble in both tetrahydrofuran and acetone, and precipitated very well, giving a light brown, fibrous material. Phosphorylation of compound 7 is indicated by the IR spectrum, which reveals disappearance of the O—H peak and a shifting of the P=N/P=O stretch to 1318 cm$^{-1}$. A difference in the relaxation times of the backbone and side group phosphorus is detected from the $^{31}$P NMR spectra. The integration ratio of the backbone to side group phosphorus atoms decreased from 3.2, with a receiver delay of 1 second, to a ratio of 2.2 with a receiver delay of 10 seconds.

Compound 11

Phosphorylation of Compound 7 with diphenyl chlorophosphate to yield [N=P(OC$_6$H$_4$OP(O)(OC$_6$H$_5$)$_2$)$_2$]$_n$ Compound 7 (0.75 g) is dissolved in 200 mL THF, and 1.2 mL (1.5 eq) of triethylamine is added. The solution is cooled to 0° C., and then 0.01 g CuCl is added. A solution of 3.27 g (2 eq) diphenyl chlorophosphate in 30 mL THF is added dropwise. The mixture is maintained at 0° C. for 3 hours, allowed to warm to room temperature, and then refluxed for 12 hours. After completion of the reaction, the mixture is concentrated by rotary evaporation and precipitated into distilled water. It is then purified by precipitation into distilled water twice and hexane twice and then dried under vacuum to yield a light brown, fibrous material. Yield: 1.1 g (79%). $^{31}$P NMR (CDCl$_3$) δ –19.3 ppm (P=N), –17.0 ppm ((RO)$_3$P=O); $^1$H NMR (CDCl$_3$) δ 7.0 ppm (8H, br, Ar), 6.8 ppm (4H Ar AA' BB'), 6.6 ppm (2H, Ar); $^{13}$C NMR (CDCl$_3$) δ 150.2, 148.1, 146.7, 129.7, 125.4, 121.8, 120.9, 119.9 ppm (Ar). IR (cm$^{-1}$): 3081, 1601, 1498, 1318, 1190, 965, 850. $T_g$=–11.5° C.

Phosphorylation of Bromo Functionalized Phosphazenes

Halogenated phosphate esters also can be employed to phosphorylate bromo functionalized phosphazenes such as compounds 5 and 6 to produce compounds 12–15. Reaction of halogenated phosphate esters with bromo functionalized phosphazene advantageously enables formation of phosphonates.

Compound 12

Phosphorylation of Compound 5 with diethyl chlorophosphate.

Cyclic trimer compound 5 (0.30 g) is dissolved in 75 mL THF and cooled to –78° C. To this solution is added slowly 1.4 mL (1.5 eq) butyllithium solution, and the resultant cloudy mixture is stirred at –78° C. for 1 hour. A solution of 0.53 g (2 eq) diethyl chlorophosphate in 10 mL THF is then added dropwise. The resultant cloudy yellow mixture is maintained at –78° C. for three hours and then allowed to warm to room temperature overnight. The mixture is concentrated by rotary evaporation and treated with a large excess of distilled water. The brown, oily product is redissolved in THF and treated with water twice, treated with hexane twice, dissolved in methanol, and treated with water, and then dried under vacuum. Yield: 0.2 g. $^{31}$P NMR (CDCl$_3$) δ 18.2 ppm (m, (RO)$_2$RP=O), 8.3 ppm (P=N); 1H NMR (CDCl$_3$) δ 7.7 ppm (2H,m, Ar), 7.2 ppm (3H, Ar) 6.8 ppm (1H, m, Ar), 4.1 ppm (4H, m, OCH$_2$—), 1.3 ppm (6H, m, CH$_3$); $^{13}$C NMR (CDCl$_3$) δ 153.5, 133.6, 129.5, 125.3, 120.9 ppm (Ar), 62.2 (OCH$_2$—), 16.3 (CH$_3$). IR (cm$^{-1}$): 3467, 2983, 1593, 1493, 1419, 1245, 1203, 1184, 1130, 1022, 949, 887, 736. MH$^+$=1510.

Compound 13

Phosphorylation of Compound 5 with diphenyl chlorophosphate.

A solution of compound 5 is formed by dissolving (0.30 g) of compound 5 in 75 mL THF and cooling to –78° C. To this solution is slowly added 1.4 mL (1.5 eq) butyllithium solution, and the resultant cloudy mixture is stirred at –78° C. for 1 hour. A solution of 0.83 g (2 eq) diphenyl chlorophosphate in 10 mL THF is then added dropwise. The mixture is maintained at –78° C. for three hours and then allowed to warm to room temperature overnight. The mixture is concentrated by rotary evaporation and treated with a large excess of distilled water. The resulting white solid is dissolved in toluene and treated with diethyl ether twice, and then dried under vacuum. Yield: 0.1 g. $^{31}$P NMR (CDCl$_3$) δ 10.7 ppm (m,(RO)$_2$RP=O), 8.1 ppm (P=N); $^1$H NMR (CDCl$_3$) δ 7.9 ppm (3H, Ar), 7.2 ppm (16H, Ar); $^{13}$C NMR (CDCl$_3$) δ 134.2, 129.8, 129.1, 125.3, 121.3, 120.5 ppm (Ar). IR (cm$^{-1}$): 3070, 2920, 1591, 1491, 1271, 1186, 1165, 1130, 943, 887, 773. MH+=2087.

Compound 14

Phosphorylation of compound 6 with diethyl chlorophosphate.

Compound 6 (0.75 g) is first dissolved in refluxing dioxane, evaporated to dryness under reduced pressure, and then dissolved in 600 mL THF. The solution is cooled to 78° C., and then 4.8 mL (2 eq) butyllithium solution is added slowly. The resultant cloudy mixture is stirred at –78° C. for 1 hour. A solution of 1.73 g (2.6 eq) diethyl chlorophosphate in 30 mL THF is then added dropwise. The mixture is maintained at 78° C. for three hours and then quenched by the dropwise addition of 10 mL distilled water, at which point the product precipitated from solution. The mixture is warmed to room temperature and filtered, giving a white solid in large chunks. The product is washed with hot THF, dioxane, and DMF and dried under vacuum. Yield=0.4 g. IR (cm$^{-1}$): 3280, 3200–2800, 1601, 1492, 1402, 1216, 1100, 1056, 947, 844, 774.

Compound 15

Phosphorylation of compound 6 with diphenyl chlorophosphate.

Compound 6 (0.75 g) is first dissolved in refluxing dioxane, evaporated to dryness under reduced pressure, and then dissolved in 600 mL THF. The solution is cooled to –78° C. To this solution is slowly added 4.8 mL (2 eq) butyllithium solution, and the resultant cloudy mixture is stirred at 78° C. for 1 hour. A solution of 2.61 g (2.6 eq) diethyl chlorophosphate in 10 mL THF is then added dropwise. The mixture is maintained at –78° C. for three hours and then quenched by the dropwise addition of 10 mL distilled water, at which point the product precipitated from solution. The mixture is warmed to room temperature and filtered to give a white solid. The product is washed with distilled water, hot THF, toluene, ethanol, and DMF and dried under vacuum. Yield: 0.2 g. IR (cm$^{-1}$): 3300–3150, 2966, 1601, 1492, 1389, 1280, 1216, 1120, 1030, 934, 844, 767.

Thermal Stability of Polyphosphazenes

The thermal stability of polyphosphazenes and phosphorylated polyphosphazenes is evaluated by thermal gravimetric analysis. Thermal weight loss measurements of the polyphosphazenes are made using a Perkin Elmer TGA-7 under an atmosphere of dry nitrogen at a flow rate of 30 cc/min using a heating rate of 20° C./min. Glass transition temperatures are measured using a Perkin-Elmer DSC-7 system. Thermal weight loss measurements of the polystyrene films are made using a SSC 5200 Haak-Buchner thermogravimetric analyzer equipped with a HP model 712/60 Power Risk Station under an atmosphere of compressed air at a flow rate of 30 cc/min using a heating rate of 20° C./min. The results are shown in Table 1.

TABLE 1

| Compound | Temp. (° C.) @ 1% weight Loss of sample | Temp. (° C.) @ 5% weight Loss of sample | Temp. (° C.) @ 10% weight Loss of sample | Char @ 700° C. (wt. %) |
|---|---|---|---|---|
| 3 | 285 | 355 | 374 | 50.5 |
| 4 | 358 | 415 | 428 | 49.3 |
| 6 | 262 | 415 | 449 | 25.6 |
| 7 | 110 | 218 | 380 | 50.1 |
| 10 | 111 | 190 | 233 | 48.3 |
| 11 | 376 | 476 | 487 | 40.7 |

The phosphorylated phosphazenes of the invention are evaluated for use as flame retardant additives in organic polymers such as polystyrene. Although the use of phosphorylated phosphazenes of the invention is illustrated below in connection with use in polystyrene, it is to be understood that the phosphorylated phosphazenes of the invention may be used to improve the fire resistance properties of a wide variety of organic polymers. Examples of these polymers include, but are not limited to, methyl methacrylate, polycarbonate, nylon, polyester, polyurethane, polyethylene, and polypropylene, as well as blends and copolymers thereof.

Polystyrene Blends

Polystyrene blends are prepared by mixing phosphorylated phosphazene with polystyrene. The phosphorylated phosphazene is chosen in accordance with the type of blend desired. Where a homogeneous blend is desired, then a low MW cyclic phosphorylated phosphazene trimer preferably is added to the polystyrene. If a composite material blend is desired, then a high MW phosphorylated polyphosphazene high polymer is added to the polystyrene. High MW phosphorylated polyphosphazene high polymers typically have 100–1000 units repeating units and a number average molecular weight of about 10,000 to 200,000.

Miscibility of phosphorylated phosphazenes in polystyrene

To assess the extent of miscibility of phosphorylated phosphazenes in polystyrene, triphenyl phosphate, product 8 and product 9 are each individually mixed with polystyrene at 0, 10, 20, and 30 wt % to achieve a total solids content of 5 g. The resulting mixtures are dissolved in 50 mL methyl ethyl ketone ("MEK") and cast into molds measuring 22.5 cm×17.5 cm. Films are obtained by slow evaporation of the MEK solvent by covering both the mold and an adjacent reservoir of pure MEK with a loose covering of aluminum foil. Five hours after film formation, the films are dried in a vacuum oven at 40° C. for 72 hours to produce 0.15 mm thick films. Mixtures such as polystyrene-triphenyl phosphate, and polystyrene-product 9 which form transparent films are considered miscible. Mixtures such as polystyrene-product 8 which form opaque films are considered immiscible.

Flame Resistance of Polystyrene Blends

In order to evaluate the flame retardant effects of the phosphorylated compounds of the invention, polystyrene blends having compounds 8 and 9 at 10, 20, and 30 wt % levels are compared to polystyrene blends having triphenyl phosphate 10, 20, and 30 wt % levels. All amounts are based on the weight of polystyrene. These blends are evaluated for flame resistance by measuring their respective oxygen indices. Oxygen indices are obtained on an instrument constructed according to the specifications of standard ASTM-D-2863-91 using Type D specimens. The compositions and the oxidation indices of the blends is shown Table 2.

TABLE 2

| Sample NO. | Additive | Wt. %[1] | OI[2] | Temp. @ 1% weight loss of sample | Temp. @ 5% weight loss of sample | Temp. @ 10% weight loss of sample | Char @ 650° C. |
|---|---|---|---|---|---|---|---|
| 1 | none | 0 | 18 | 168 (° C.) | 297 (° C.) | 315 (° C.) | 0.1 (wt. %) |
| 2 | Triphenyl phosphate | 10 | 22 | 177 | 263 | 307 | 0.2 |
| 3 | Triphenyl phosphate | 20 | 24 | 205 | 255 | 292 | 0.2 |
| 4 | Triphenyl phosphate | 30 | 27 | 198 | 233 | 255 | 1.5 |
| 5 | Compound 8 | 10 | 19 | 166 | 292 | 323 | 2.0 |
| 6 | Compound 8 | 20 | 20 | 169 | 287 | 320 | 5.4 |
| 7 | Compound 8 | 30 | 22 | 180 | 282 | 307 | 10.6 |
| 8 | Compound 9 | 10 | 24 | 220 | 328 | 350 | 1.1 |
| 9 | Compound 9 | 20 | 26 | 195 | 337 | 375 | 3.9 |
| 10 | Compound 9 | 30 | 25 | 226 | 333 | 376 | 10.1 |

[1]Wt. % Additive in Polystyrene
[2]Oxidation Index of Polystyrene with Additive.

As shown in Table 2, polystyrene-triphenyl phosphate compositions of examples 2–4 have excellent flame retardant behavior as seen by the increase in Oxygen Index (OI). Sample 4 that has 30 wt % triphenyl phosphate has its glass transition at room temperature, resulting in a film that is very pliable.

The polystyrene-compound 9 compositions of samples 8–10, however, have flame retardant properties which are superior to the polystyrene-triphenyl phosphate compositions. The superior flame retardant properties of compound 9 are evident from the OI values in Table 2. Polystyrene compositions which include 10 and 20 wt % of compound 9 have increased OI relative to polystyrene compositions which include the same amounts of triphenyl phosphate. Compound 9 also has only a slight plasticizing effect on polystyrene as compared to triphenyl phosphate. Sample 10 that has 30 wt % compound 9 has a glass transition temperature that is well above room temperature.

Samples 5–7 which contain phosphorylated phosphazene compound 8 also improve the fire resistance of polystyrene. The glass transition temperature of polystyrene is unaffected by presence of compound 8 in amounts of from about 10 to about 30 wt %. This is also indicative of immiscibility of compound 8 with polystyrene.

We claim:

1. A method of making phosphorylated phosphazenes having improved thermal stability comprising,
reacting an aryloxy-hydroxy functional phosphazene with a halogenated chlorophosphate selected from the group consisting of aliphatic chlorophosphates and aromatic chlorophosphates.

2. The method of claim 1 wherein the aryloxy-hydroxy functional phosphazene is selected from the group consisting of hexakis(4-hydroxyphenoxy)cyclotriphosphazene and poly[bis(4-hydroxyphenoxy)phosphazene].

3. The method of claim 2 wherein the aliphatic chlorophosphate is selected from the group consisting of alkyl chlorophosphates, alkyne chlorophosphate, and alkene chlorophosphates.

4. The method of claim 3 wherein the alkyl chlorophosphates are selected from the group consisting of C1–C6 straight chain alkyl chlorophosphates, C1–C6 branched alkyl chlorophosphates, and C1–C6 cyclic alkyl chlorophosphates.

5. The method of claim 3 wherein the alkyne chlorophosphates is any one of C3–C8 alkyne chlorophosphates.

6. The method of claim 3 wherein the alkene chlorophosphates is any one of C3–C8 alkene chlorophosphate.

7. The method of claim 4 wherein the alkyl chlorophosphate is ethyl chlorophosphate.

8. The method of claim 2 wherein the aromatic chlorophosphates are selected from the group consisting of phenyl chlorophosphate, C1–C6 alkyl substituted phenyl chlorophosphate, C3–C8 alkyne substituted phenyl chlorophosphate, and C3–C8 alkene substituted phenyl chlorophosphate.

9. The method of claim 8 wherein the aromatic chlorophosphate is phenyl chlorophosphate.

10. A phosphorylated polyphosphazene having improved thermal stability comprising the reaction product of an aryloxy-hydroxy functionalized phosphazene and a halogenated chlorophosphate selected from the group consisting of aliphatic chlorophosphate and aromatic chlorophosphates.

11. The polyphosphazene of claim 10 wherein the aryloxy-hydroxy functional phosphazene is selected from the group consisting of hexakis(4-hydroxyphenoxy) cyclotriphosphazene and poly[bis(4-hydroxyphenoxy) phosphazene].

12. The polyphosphazene of claim 11 wherein the aliphatic chlorophosphate is selected from the group consisting of alkyl chlorophosphates, alkyne chlorophosphate, and alkene chlorophosphates.

13. The polyphosphazene of claim 12 wherein the alkyl chlorophosphates are selected from the group consisting of C1–C6 straight chain alkyl chlorophosphates, C1–C6 branched alkyl chlorophosphates, and C1–C6 cyclic alkyl chlorophosphates.

14. The polyphosphazene of claim 12 wherein the alkyne chlorophosphates is any one of C3–C8 alkyne chlorophosphates.

15. The polyphosphazene of claim 12 wherein the alkene chlorophosphates is any one of C3–C8 alkene chlorophosphate.

16. The polyphosphazene of claim 13 wherein the alkyl chlorophosphate is ethyl chlorophosphate.

17. The polyphosphazene of claim 11 wherein the aromatic chlorophosphates are selected from the group consisting of phenyl chlorophosphate, C1–C6 alkyl substituted phenyl chlorophosphate, C3–C8 alkyne substituted phenyl chlorophosphate, and C3–C8 alkene substituted phenyl chlorophosphate.

18. The polyphosphazene of claim 17 wherein the aromatic chlorophosphate is phenyl chlorophosphate.

19. An organic polymeric mixture having improved fire resistance comprising an organic polymer and a phosphorylated phosphazene wherein the phosphorylated phosphazene is the reaction product of an aryloxy-hydroxy functional phosphazene and a halogenated chlorophosphate selected from the group consisting of aliphatic chlorophosphate and aromatic chlorophosphates.

20. The polymeric mixture of claim 19 wherein the aryloxy-hydroxy functional phosphazene is selected from the group consisting of hexakis(4-hydroxyphenoxy) cyclotriphosphazene and poly[bis(4-hydroxyphenoxy) phosphazene].

21. The polymeric mixture of claim 20 wherein the aliphatic chlorophosphate is selected from the group consisting of alkyl chlorophosphates, alkyne chlorophosphate, and alkene chlorophosphates.

22. The polymeric mixture of claim 21 wherein the C1–C6 alkyl chlorophosphates are selected from the group consisting of C1–C6 straight chain alkyl chlorophosphates, C1–C6 branched alkyl chlorophosphates, and C1–C6 cyclic alkyl chlorophosphates.

23. The polymeric mixture of claim 21 wherein the alkyne chlorophosphates is any one of C3–C8 alkyne chlorophosphates.

24. The polymeric mixture of claim 21 wherein the alkene chlorophosphates is any one of C3–C8 alkene chlorophosphate.

25. The polymeric mixture of claim 22 wherein the alkyl chlorophosphate is ethyl chlorophosphate.

26. The polymeric mixture of claim 20 wherein the aromatic chlorophosphates are selected from the group consisting of phenyl chlorophosphate, C1–C6 alkyl substituted phenyl chlorophosphate, C3–C8 alkyne substituted phenyl chlorophosphate, and C3–C8 alkene substituted phenyl chlorophosphate.

27. The polymeric mixture of claim 26 wherein the aromatic chlorophosphate is phenyl chlorophosphate.

28. The polymeric mixture of claim 27 wherein the organic polymer is polystyrene.

29. An organic polymeric mixture having improved fire resistance consisting essentially of an organic polymer and a phosphorylated phosphazene, wherein the phosphorylated phosphazene is the reaction product of an aryloxy-hydroxy functional phosphazene a halogenated chlorophosphate selected from the group consisting of aliphatic chlorophosphate and aromatic chlorophosphates.

30. The mixture of claim 29 wherein the aryloxy-hydroxy functional phosphazene is selected from the group consisting of hexakis(4-hydroxyphenoxy)cyclotriphosphazene and poly[bis(4-hydroxyphenoxy)phosphazene].

31. The mixture of claim 30 wherein the aliphatic chlorophosphate is selected from the group consisting of alkyl chlorophosphates, alkyne chlorophosphate, and alkene chlorophosphates.

32. The mixture of claim 31 wherein the C1–C6 alkyl chlorophosphates are selected from the group consisting of C1–C6 straight chain alkyl chlorophosphates, C1–C6 branched alkyl chlorophosphates, and C1–C6 cyclic alkyl chlorophosphates.

33. The mixture of claim 31 wherein the alkyne chlorophosphates is any one of C3–C8 alkyne chlorophosphates.

34. The mixture of claim 31 wherein the alkene chlorophosphates is any one of C3–C8 alkene chlorophosphate.

35. The mixture of claim 32 wherein the alkyl chlorophosphate is ethyl chlorophosphate.

36. The mixture of claim 30 wherein the aromatic chlorophosphates are selected from the group consisting of phenyl chlorophosphate, C1–C6 alkyl substituted phenyl chlorophosphate, C3–C8 alkyne substituted phenyl chlorophosphate, and C3–C8 alkene substituted phenyl chlorophosphate.

37. The mixture of claim 36 wherein the aromatic chlorophosphate is phenyl chlorophosphate.

38. The mixture of claim 37 wherein the organic polymer is polystyrene.

* * * * *